United States Patent [19]

Lott et al.

[11] Patent Number: 5,074,293

[45] Date of Patent: Dec. 24, 1991

[54] WOUND DRESSING HAVING PEELING-FORCE VARYING RELEASE LINERS

[75] Inventors: Gloria Y. Lott, Des Peres; Scott M. Britton, Ballwin, both of Mo.; Barry E. Constantine, Island Heights, N.J.

[73] Assignee: Sherwood Medical Company, St. Louis, Mo.

[21] Appl. No.: 519,373

[22] Filed: May 4, 1990

Related U.S. Application Data

[63] Continuation of Ser. No. 278,256, Nov. 30, 1988, Pat. No. 4,926,850.

[51] Int. Cl.⁵ .................. A61F 13/00; A61F 15/00; A61L 13/00
[52] U.S. Cl. .................. 128/155; 206/441; 128/156
[58] Field of Search .................. 128/83, 155, 156, 169, 128/893, 894; 604/307, 389, 390; 206/440, 441

[56] References Cited

U.S. PATENT DOCUMENTS

| | | | |
|---|---|---|---|
| 3,811,438 | 5/1974 | Economou | 128/156 |
| 3,916,887 | 11/1975 | Kelly | 128/132 D |
| 4,212,296 | 7/1980 | Schaar | 128/156 |
| 4,265,234 | 5/1981 | Schaar | 128/156 |
| 4,316,456 | 2/1982 | Stoneback | 128/132 D |
| 4,372,303 | 2/1983 | Grossmann et al. | 128/132 D |
| 4,513,739 | 4/1985 | Johns | 128/156 |
| 4,614,183 | 9/1986 | McCracken et al. | 128/132 R |
| 4,744,355 | 5/1988 | Faasse, Jr. | 128/156 |
| 4,926,850 | 5/1990 | Lott et al. | 128/155 |
| 4,928,680 | 5/1990 | Sandbank | 128/155 |

Primary Examiner—Randall L. Green
Assistant Examiner—Paul Prebilic
Attorney, Agent, or Firm—Andrew J. Beck; Montgomery W. Smith; Gene B. Kartchner

[57] ABSTRACT

A wound dressing comprises a vapor permeable plastic film coated on one side with an adhesive about the periphery of a wound contacting window in the central portion of the dressing. A pair of release liners covers the adhesive coating and include tabs so that the release liners can be peeled from the adhesive coating. Strips are provided adjacent to and at opposite lateral sides of the wound contacting window to change abruptly the resistance to peeling of the release liners from the adhesive coated film. Accordingly, when the user feels this change in resistance, he or she knows that the wound contacting window and a small portion of the adhesive about the periphery thereof is uncovered which allows the dressing to be anchored about the patient's wound with the release liners partially in place and the wound contacting window exposed. This minimizes the tendency of the film to wrinkle and/or to fold on itself such that the adhesive adheres to itself.

23 Claims, 1 Drawing Sheet

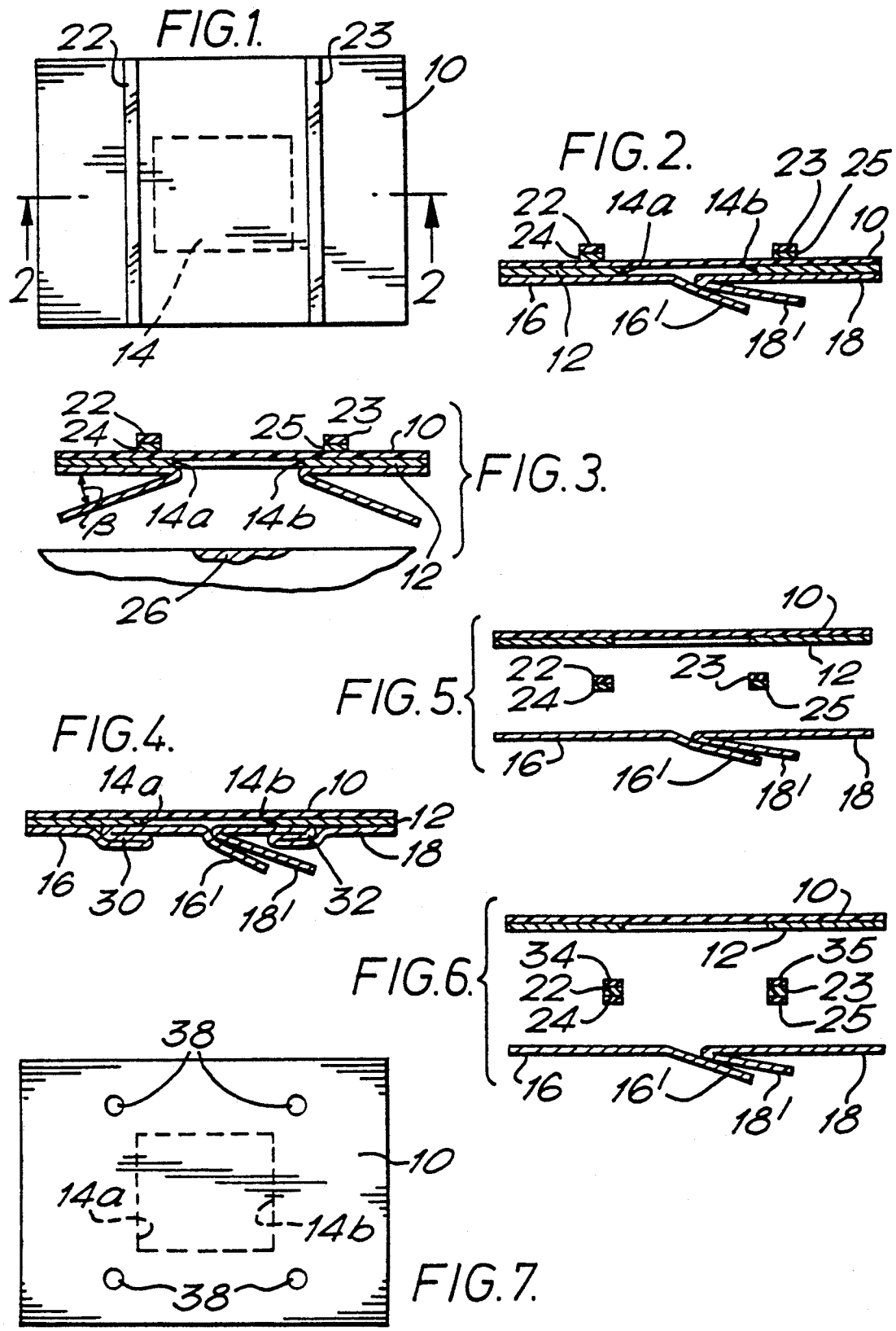

5,074,293

WOUND DRESSING HAVING PEELING-FORCE VARYING RELEASE LINERS

This is a continuation of copending application Ser. No. 07/278,256 filed on Nov. 30, 1988 now U.S. Pat. No. 4,926,850.

This invention relates to wound dressings and, in particular, to a vapor permeable, plastic film dressing having an improved release liner which facilitates application of the dressing to a patient's wound.

BACKGROUND

Adhesive backed, vapor permeable, plastic film wound dressings are sold in various sizes and shapes. Typically, they include a very thin vapor permeable plastic film or backing sheet coated with a medical grade adhesive (e.g. an acrylic adhesive). In some dressings, the adhesive surrounds an uncoated central window which may or may not include an absorbent pad (usually gauze) to cover the wound. The adhesive coating is covered usually by two relatively rigid release liners each of which covers one-half of the dressing. The release liners support the film, protect the adhesive coated areas of the dressing, and help preserve sterility. When the dressing is to be used, the release liners are peeled from the adhesive and the dressing then applied to the wound. Examples of such dressings are those sold by Sherwood Medical Company under the trademarks BLISTERFILM ® and VIASORB ®.

A problem with dressings of the type described is that upon removal of the release liners, the very thin plastic film has a tendency to wrinkle, making it difficult to apply the dressing uniformly to the patient's skin. Furthermore, particularly in the case of relatively large dressings, if the adhesive surface should accidentally fold over and adhere to itself, it becomes difficult, if not impossible, to flatten the dressing so that it can be applied in a flattened condition to a patient. In some cases a badly wrinkled dressing must be discarded.

OBJECTS OF THE INVENTION

The principle object of the invention is to provide an improved adhesive backed dressing wherein the likelihood of wrinkling and inadvertent contact between adhesive portions is substantially reduced.

A further object of the invention is to provide an improved dressing of the type described wherein positioning of the dressing relative to the wound is facilitated.

SUMMARY OF THE INVENTION

In accordance with the invention, a dressing comprises a vapor permeable, plastic backing film coated on one side with an adhesive but including an uncoated wound contacting window, for example at the central portion of the bandage. Release liner means cover the adhesive coating and include grasping means so that the release liners can be peeled from the adhesive coating. Means are provided spaced from but adjacent at least one lateral side of the wound contacting window to change abruptly the resistance to peeling of the release liner means from the adhesive coated plastic film. When the user feels this change in resistance, he or she knows that the wound contacting window and only a small portion of the adhesive coating is uncovered. The dressing can then be applied about the patient's wound with the release liner means partially in place and the wound contacting portion and only a portion of the adhesive coating exposed. This minimizes the tendency of the plastic film to wrinkle and/or to fold on and adhere to itself.

THE DRAWINGS

FIG. 1 is a diagrammatic plan view of a dressing according to a preferred embodiment of the invention;

FIG. 2 is a diagrammatic sectional view along the line 2—2 of FIG. 1;

FIG. 3 is a sectional view similar to FIG. 2 showing the release liners partially peeled from the dressing immediately prior to its application to a wound;

FIG. 4 is a diagrammatic sectional view of a dressing according to a second embodiment of the invention;

FIG. 5 is a diagrammatic sectional view of a dressing according to a third embodiment of the invention;

FIG. 6 is a diagrammatic sectional view of a dressing according to a fourth embodiment of the invention; and FIG. 7 is a diagrammatic plan view of a dressing according to a fifth embodiment of the invention.

DETAILED DESCRIPTION

The principles of the invention are applicable to different dressing constructions. In particular, the invention is applicable to dressings with and without wound patches or gauze at a central portion thereof. For purposes of explanation, FIGS. 1-7 illustrate the invention in conjunction with the Sherwood Medical BLISTERFILM dressing which includes no wound patch or gauze.

Referring to FIGS. 1 and 2, a dressing or bandage in accordance with the invention comprises a vapor permeable plastic film or backing sheet 10 (for example made of polyurethane) coated on most of one surface with an adhesive 12. Adhesive 12 may be a standard medical grade acrylic adhesive. The central portion of the backing sheet 10 is not coated with the adhesive thus forming a non-adhesive window 14 which is intended to overlie and sometimes contact the wound to which the dressing is applied. In this type of dressing the window is surrounded by adhesive on all four of its sides.

As indicated above, the dimensions of the dressing can vary substantially. One example of a common dressing would be an 18 cm × 18 cm square polyurethane film with a thickness between .0005 and .002 inches. The wound contacting window would be located in the center of the dressing and have dimensions of 10 cm × 10 cm.

A pair of release liners 16 and 18 are applied to the adhesive 12 but a single liner, not shown, could be utilized in a known manner. Release liners 16 and 18 prevent draping or wrinkling of the film 10 and facilitate exertion of tension on the film to achieve flat application thereof. The liners also prevent inadvertent adhesion of the adhesive to itself as well as other surfaces, and function to maintain the sterility of the wound contact area of the dressing. The liners 16 and 18 include tabs 16' and 18' which can be grasped by a user to peel the release liners from the dressing when it is to be applied to a patient. In actual practice, tabs 16' and 18' will lie flat on the dressing prior to use. By way of example, the release liners 16 and 18 may be made of 60-90 pound silicone coated kraft paper.

The invention provides a simple way of "signaling" the user of the dressing when the release liner has been peeled to just past the opposite lateral sides of the window 14, in this case lateral edges 14a and 14b, exposing only a small portion of the adhesive coating adjacent such sides and about the full periphery of the window, prior to application to a wound 26 (FIG. 3). According to the preferred embodiment of the invention, such means comprises elongated relatively stiffer plastic strips 22 and 23 adhered to the non-adhesive surface of the film 10 (the upper surface in FIG. 2) by adhesive strips 24 and 25. In the preferred embodiment, strips 22 and 23 are made of Mylar and adhesive strips 24 and 25 comprise a medical grade acrylic adhesive.

The Mylar strips 22 and 23 function to increase abruptly the resistance to peeling of the release liners, i.e. the peel force required to remove release liners 16 and 18 from the dressing when the release liners are peeled to just past the lateral edges 14a and 14b of window 14 as shown in FIG. 3 The peel force required to remove the release liners 16 and 18 depends on the adhesive forces between adhesive layer 12 and release liners 16 and 18 as well as the characteristics of the backing sheet 10. The plastic strips 22 and 23 increase the rigidity of the backing sheet 10 in the areas immediately beneath the strips 22 and 23. Because of this increased rigidity, when the release liners 16 and 18 are peeled just past or beyond the edges 14a and 14b of window 14, the peel angle (shown as 13 in FIG. 3) decreases (for example, from about 90° to about 30°) which means that the component of force in a vertical direction tending to pull the release liner from the adhesive coating decreases. This in turn means that a greater pulling force is required to peel the release liners. When this occurs, the user feels an abrupt change in the resistance of the liners to peeling.

It is preferred that the Mylar strips 22 and 23 be placed so as to be spaced from and just beyond the lateral edges 14a and 14b of window 14 as shown in FIGS. 1 and 2 with a narrow strip of adhesive between the strips 22 and 23 and the edges 14a and 14b. At these locations the window is fully uncovered and the additional adhesive encountered by the release liners 16 and 18 (i.e. the adhesive adjacent to the lateral edges of window 14) increases to a small extent the peeling force required, which is substantially increased upon encounter with the area of the adhesive beneath the strips 22 and 23 to provide the signal to the user that the window and a small portion of the adhesive adjacent the lateral side of the window has been uncovered. The strips 22 and 23 should extend across the entire width of the dressing as shown in FIG. 1. The width and thickness of the strips affect their rigidity, but these dimensions are variable over a substantial range. Currently, it is believed that the width of strips 22 and 23 should be between about 1/16 inch and ⅜ inch depending also on the size of the dressing. The thickness depends on the stiffness of the material used. In the case of Mylar strips, .001 inch has been used successfully. Preferably, in the case of Mylar, the thickness should be no greater than .010 inches.

To use the dressing shown in FIGS. 1 and 2, the user grasps the tab 16' and 18' and starts to peel the release liners from the adhesive backing 10. Upon peeling the release liners to the Mylar strips 22 and 23 at the lateral edges of window 14 (FIG. 3), substantial increased resistance is felt thereby signaling to the user that the release liners have been peeled sufficiently to expose window 14. When this happens, the user releases tabs 16' and 18' and places the dressing over the wound 26 with adhesive contacting the skin about the full periphery of the window. Since the Mylar strips 22 and 23 define the lateral edges of window 14, and a small strip of adhesive adjacent thereto, placement of the window with respect to the wound is facilitated without uncovering more adhesive than is necessary to initially anchor the window. When the dressing is in place, it can be anchored by applying pressure to the adhesive at the lateral sides and above and below the window 14 (as viewed in FIG. 1) to initially hold the dressing in its desired position. Thereafter, the remaining portions of the release liners 16 and 18 may be peeled from the adhesive and the possibility of wrinkling of the dressing is substantially reduced because the laterally inward portion of the dressing adjacent the window, is anchored flat. Since the dressing is properly positioned and anchored on the patient when the release liners are removed from the remainder of the adhesive coating, the tendency of the backing 10 to wrinkle or to fold back on itself is significantly reduced.

The preferred embodiment shown in FIGS. 1 and 2 operates by providing a signal to the user when the release liners have been peeled to expose window 14 by causing an abrupt increase in the force required to remove the release liners. It is also possible to provide a signal to the user by causing an abrupt decrease in this force. A dressing construction in which this occurs is shown in FIG. 4. In this embodiment, the release liners 16 and 18 include respective Z folds 30 and 32 positioned at the lateral edges 14a and 14b of window 14. When release liners 16 and 18 are peeled to apply the dressing, exposure of the Z fold causes an abrupt decrease in the resistance to peeling of the liners. This decreased resistance then signals to the user that the window and a portion of the adhesive about the periphery thereof are exposed and the dressing ready to be initially anchored after which the remainder of the liners are peeled away.

In the embodiment shown in FIG. 4, when the lateral edge adjacent the wound contacting window 14 is reached, the force required to peel the release liner from the adhesive layer 12 does not actually decrease but it feels to the user as though it has because the folded portions 30 and 32 open with virtually no resistance. The actual force thereafter required to peel the release liner from the adhesive layer remains the same. Nevertheless, as used herein, reference to a change in resistance to peeling or in the force required to peel the release liners from the adhesive coating 12 is intended to include a perceived change as well as an actual change, for example, as occurs in the remaining embodiments.

FIGS. 5, 6, and 7 show three additional embodiments in which the resistance to peeling is increased as a signal to the user. In FIG. 5, the plastic strips 22 and 23 are positioned between the adhesive coating 12 and the release liners 16 and 18 with the adhesive strips 24 and 25 securing plastic strips 22 and 23 to the liners 16 and 18, respectively. When the liners 16 and 18 are peeled to the position of strips 22 and 23, the adhesion between the strips 22 and 23 and adhesive coating 12 causes increased resistance to peeling. In this embodiment, the adhesive strips 24 and 25 must provide adhesion to release liners 16 and 18 greater than the adhesive bonds between the plastic strips 22, 23 and adhesive layer 12 so that strips 22 and 23 are removed from the dressing with the release liners 16 and 18 after the dressing is positioned over the wound.

The embodiment of FIG. 6 is similar to that of FIG. 5 with the addition of silicone release strips 34 and 35 between strips 22 and 23, respectively, and adhesive coating 12. The release strips 34 and 35 ensure that the plastic strips 24 and 25 will be removed from the dressing with the release liners 16 and 18, yet provide sufficient adhesion to the adhesive coating 12 so that the signal of increased resistance is provided.

FIG. 7 shows an embodiment in which increased resistance to peeling is provided by four sonically welded areas 38. As is well-known, the application of an ultrasonic field to an adhesive layer can increase the tack of the adhesive in those areas subject to the field. Thus, in FIG. 7, increased peel resistance is encountered when the liners are peeled to the sonic welds 38. Instead of using four sonic welds, sonic welds in the form of strips just beyond the lateral edges 14a and 14b of the window 14 may also be used.

We claim:

1. A dressing comprising:
a plastic film having a wound contacting portion and lateral ends;
an adhesive coating on one surface of said plastic film about said wound contacting portion providing an adhesive-free wound contacting window;
release liner means covering at least a portion of said adhesive coating and at least a portion of said wound contacting window of said plastic film, said release liner means being in releasable contact with said adhesive coating and including grasping means for enabling said release liner means to be peeled from said adhesive coating; and
means laterally outward of at least one lateral side of said wound contacting window and remote from said lateral ends of said plastic film for varying abruptly the force required to peel said release liner means from said adhesive coating thereby providing a signal to the user when said release liner means have been peeled sufficiently to uncover said wound contacting window and a portion of said adhesive coating immediately outward of said wound contacting window.

2. A dressing comprising:
a plastic film having a wound contacting portion and lateral ends;
an adhesive coating on one surface of said plastic film about said wound contacting portion providing an adhesive-free wound contacting window and requiring a first force for overcoming the adhesive resistance of said adhesive coating laterally outward of said wound contacting window;
release liner means covering at least a portion of said adhesive coating and at least a portion of said wound contacting window of said plastic film, said release liner means being in releasable contact with said adhesive coating and including grasping means for enabling said release liner means to be peeled from said adhesive coating; and
means laterally outward of at least one lateral side of said wound contacting window and spaced from said lateral ends of said plastic film for requiring a second force for overcoming the adhesive resistance of said adhesive coating to peel said release liner means from said adhesive coating, said second force varying abruptly from said first force to provide a signal to the user when said release liner means have been peeled at least sufficiently to uncover said wound contacting window.

3. A dressing according to claim 2 wherein said release liner means comprises a pair of release liners and said means for requiring a second force are provided laterally outward of each lateral side of said wound contacting window.

4. A dressing according to claim 2 wherein said means for requiring a second force increases the force required to peel said release liner means from said adhesive coating.

5. A dressing according to claim 2 wherein said means for requiring a second force decreases the force required for laterally outboard movement of said release liner.

6. A dressing according to claim 4 wherein said means for requiring a second force further comprises first and second strips adhered to said plastic film opposite said one adhesive-coated surface, one of said first and second strips being positioned laterally outward of each of said lateral sides of said wound contacting window.

7. A dressing according to claim 6 wherein a laterally outward side of each of said first and second strips is laterally spaced from at least one of said lateral ends of said plastic film.

8. A dressing according to claim 4 wherein said means for requiring a second force further comprises first and second plastic strips positioned between said release liner means and said adhesive coating, one of said first and second plastic strips being positioned laterally outward of each of said lateral sides of said wound contacting window.

9. A dressing according to claim 8 further including an adhesive strip located between each of said first and second plastic strips and said release liner means, said adhesive strip forming a bond between said release liner means and said first and second plastic strips, said adhesive coating forming a bond between said first and second plastic strips and said plastic film, said bond between said release liner means and said first and second plastic strips being greater than said bond between said first and second plastic strips and said plastic film.

10. A dressing according to claim 4 wherein said means for requiring a second force comprises at least one area of increased adhesiveness of said adhesive coating positioned laterally outward of each of said lateral sides of said wound contacting window.

11. A dressing according to claim 5 wherein said means for requiring a second force comprises a fold in each of said release liners, said folds being positioned parallel to and outward of each of said lateral sides of said wound contacting window.

12. A dressing according to claim 2 wherein said wound contacting window comprises an adhesive-free portion on said plastic film and said adhesive coating is provided on said plastic film about the full periphery of said adhesivefree portion.

13. A dressing according to claim 2 wherein said wound contacting portion includes a gauze pad connected to said plastic film said gauze pad being adapted to contact the wound.

14. A dressing comprising:
a plastic film having a wound contacting portion and lateral ends;
an adhesive coating on at least a portion of one surface of said plastic film immediately laterally outward of said wound contacting portion providing an adhesive-free wound contacting window;
release liner means covering at least a portion of said adhesive coating and at least a portion of said wound contacting window of said plastic film, said release liner means being in releasable contact with said adhesive coating and including grasping means for enabling said release liner means to be peeled from said adhesive coating; and means laterally outward of at least one lateral side of said wound contacting window and spaced from said lateral ends of said plastic film for increasing abruptly the force required to peel said release liner means from said adhesive coating thereby providing a signal to the user when said release liner means have been peeled sufficiently to uncover said wound contacting window and a portion of said adhesive coating immediately outboard of said wound contacting window.

15. A dressing according to claim 14 wherein said release liner means comprises a pair of release liners and said force increasing means are provided laterally outward of each lateral side of said wound contacting window.

16. A dressing according to claim 15 wherein said force increasing means further comprises first and second strips adhered to said plastic film opposite said one adhesive-coated surface, one of said first and second strips being positioned laterally outward of each of said lateral sides of said wound contacting window.

17. A dressing according to claim 16 wherein a laterally outward side of each of said first and second strips is laterally spaced from at least one of said lateral ends of said plastic film.

18. A dressing according to claim 15 wherein said force increasing means further comprises first and second plastic strips adhered between said release liner means and said adhesive coating, one of said first and second plastic strips being positioned laterally outward of each of said lateral sides of said wound contacting window.

19. A dressing according to claim 18 further including an adhesive strip between each of said first and second plastic strips and said release liner means, said adhesive strips forming a bond between said release liner means and said first and second plastic strips, said adhesive coating also forming a bond between said first and second plastic strips and said plastic film, said bond between said release liner means and said first and second plastic strips being greater than said bond between said first and second plastic strips and said plastic film.

20. A dressing according to claim 15 wherein said force increasing means comprises at least one area of increased adhesiveness of said adhesive coating positioned laterally outward of each of said lateral sides of said wound contacting window.

21. A dressing according to claim 15 wherein said wound contacting window comprises an adhesive-free portion on said plastic film about the full periphery of said adhesive-free portion.

22. A dressing according to claim 15 wherein said wound contacting window includes a gauze pad connected to said plastic film, said gauze pad being adapted to contact the wound.

23. A dressing according to claim 15 wherein said adhesive coating extends from said wound contacting window to said lateral ends of said plastic film.

* * * * *